United States Patent [19]
Godsey et al.

[11] Patent Number: 5,888,760
[45] Date of Patent: Mar. 30, 1999

[54] UNIVERSAL TEST SYSTEMS AND METHODS OF USE THEREOF FOR IDENTIFYING MULTIPLE FAMILIES OF MICROORGANISMS

[75] Inventors: James H. Godsey, Folsom; Daniel M. Nothaft, Vacaville, both of Calif.

[73] Assignee: Dade MicroScan Inc., West Sacramento, Calif.

[21] Appl. No.: 843,634

[22] Filed: Apr. 10, 1997

[51] Int. Cl.$^6$ ............... C12Q 1/04; C12Q 1/54; C12Q 1/37; C12Q 1/44

[52] U.S. Cl. ............... 435/34; 435/14; 435/21; 435/23; 435/24; 435/19; 435/12; 435/968; 435/882; 435/885; 435/843; 435/853; 435/851; 435/871

[58] Field of Search ............... 435/34, 14, 21, 435/23, 24, 19, 12, 968, 882, 885, 843, 853, 851, 871

[56] References Cited

U.S. PATENT DOCUMENTS

| | | |
|---|---|---|
| 3,870,601 | 3/1975 | Warren et al. ............... 435/34 |
| 4,245,043 | 1/1981 | Lund ............... 435/34 |
| 4,378,438 | 3/1983 | Masaki et al. ............... 435/34 |
| 4,603,108 | 7/1986 | Bascomb ............... 435/34 |
| 4,874,695 | 10/1989 | Pincus ............... 435/34 |
| 5,055,594 | 10/1991 | Mize ............... 435/34 |
| 5,064,756 | 11/1991 | Carr et al. ............... 435/34 |
| 5,079,144 | 1/1992 | Carr et al. ............... 435/34 |
| 5,089,395 | 2/1992 | Snyder et al. ............... 435/34 |
| 5,173,434 | 12/1992 | Morris et al. ............... 435/34 |
| 5,236,827 | 8/1993 | Sussman et al. ............... 435/34 |
| 5,434,056 | 7/1995 | Monget et al. ............... 435/34 |
| 5,457,030 | 10/1995 | Badal et al. ............... 435/34 |

FOREIGN PATENT DOCUMENTS

| | | |
|---|---|---|
| 0 018 825 A1 | 4/1980 | European Pat. Off. . |
| 0-091-837 | 4/1983 | European Pat. Off. . |
| 0-326-635-B1 | 4/1988 | European Pat. Off. . |
| 0 451 775 A1 | 4/1991 | European Pat. Off. . |
| 0-451-775-B1 | 4/1995 | European Pat. Off. . |
| 1440917 | 11/1988 | U.S.S.R. . |
| 2-128-204-B | 4/1983 | United Kingdom . |
| 2 037 811 A | 7/1980 | WIPO . |
| WO 86/05206 | 9/1986 | WIPO . |

OTHER PUBLICATIONS

C. Aldridge, et al.; *Journal of Clinical Microbiology*; Automated Microbiological Detection/Identification System; 6/4: 406–413; (1977).

S. C. Edberg, et al.; *Journal of Clinical Microbiology*; Clinical Evaluation of the MICRO–ID, API 20E, and Conventional Media Systems for Identification of Enterobacteriaceae; 10/2: 161–167; (1979).

Bascomb, S., "Enzyme Tests in Bacterial Indentification", *Methods in Microbiology*, vol. 19, pp. 106–160, (1978).

Baxter MicroScan, "Rapid Gram Pos BP Combo Procedural Manual" (1992), Baxter Diagnostics, Inc., Deerfield, IL 60015–4633.

Baxter MicroScan, "Rapid Gram Negative BP Procedural Manual" (1993), Baxter Diagnostics, Inc., Deerfield, IL 60015–4633.

Baxter MicroScan, "Rapid Gram Positive Procedural Manual" (1992), Baxter Diagnostics, Inc. Deerfield, IL 60015–4633.

Manafi, M. et al., "Fluorogenic and Chromogenic Substrates Used in Baxterial Diagnostics", *Microbial Reviews*, pp. 335–348, (Sep. 1991).

Achondo, K. et al., "New Improved MicroScan Rapid Negative Identification Panel", *American Society of Microbiologists*, 1995 meeting, Washington, DC.

*Primary Examiner*—Louise N. Leary
*Attorney, Agent, or Firm*—Linda M. Buckley; Robert L. Buchanan; Lois K. Ruszala

[57] ABSTRACT

The present invention relates to a universal test systems and methods of use thereof for identifying a microorganism among at least two groups of widely divergent microorganisms. The universal test system comprises a predetermined combination of non-redundant biochemical tests comprising a substrate for at least one enzyme wherein the substrate, if acted on by the enzyme results in formation of a detectable product. Detectable products from the combination of biochemical tests are then used to identify the microorganism.

28 Claims, No Drawings

UNIVERSAL TEST SYSTEMS AND METHODS OF USE THEREOF FOR IDENTIFYING MULTIPLE FAMILIES OF MICROORGANISMS

FIELD OF THE INVENTION

The present invention relates to universal test systems and methods of use thereof to determine the identity of a microorganism which may belong to any one of multiple divergent microorganism groups, e.g., anaerobes, yeast, fastidious, enterics, staphylococcus, streptococcus, and enterococcus among microorganisms from diverse families or groups. The test systems of the present invention comprise a single battery of predetermined tests to detect the presence of enzymes unique to a microorganism family or groups, genus and/or species.

BACKGROUND OF THE INVENTION

The development of methods to classify or identify bacteria has been an ongoing goal of the microbiology community since the very beginning of the discipline of microbiology. Early methods for classification were based upon microscopic examination of the microorganism and subsequent description of their cell morphology, i.e., coccal shaped cells, rod (bacillus) shaped cells, coccal-bacillus shaped cells, budding yeasts, and sphirochytes. Microbiologists also described their microscopic observations of microorganism cell arrangements as an additional means of categorizing microorganisms, i.e., streptococcus referred to a chain of coccal shaped cells resembling a string of pearls, staphylococcus referred to a cluster of coccal shaped cells resembling a cluster of grapes, etc. Later on stains were developed to add to the differentiating capabilities of the microscope. Far most important of these was the Gram Stain which divided microorganisms into two groups; gram-negative microorganisms, which stain pink to red, and gram-positive organisms, which stained light blue to blue. It was subsequently observed that among microorganisms that cause human disease, most gram-negative microorganisms were rod shaped and most gram-positive microorganisms were coccal shaped. Another early means of differentiating microorganism was to determine the microorganism's ability to grow in the presence or absence of oxygen. Microorganisms which grow in the presence of oxygen are called aerobes and those which grow in the absence of oxygen are called anaerobes.

One of the more important early discoveries in diagnostic microbiology was the ability to grow bacteria in test tubes or in petri plates using different types of liquid or solid bacteriologic growth media. Microbiologists subsequently began to add various chemicals to the growth media to develop further means of differentiating among microorganisms, such as growth or growth inhibition tests, e.g., 6.5% NaCl inhibits the growth of streptococci but not enterococci, or biochemical tests, e.g., enteric bacteria ferment the glucose to produce acid end products while nonfermentative bacteria do not.

The combining of all of the above-mentioned morphological, growth/inhibition, and biochemical tests into a battery of tests available to microbiologists for classifying bacteria led to the development of means of classifying bacteria into the traditional taxanomic entities of family, genus, species used to classify all living things. The microbiologists' approach historically has been to develop batteries of classifying tests which are applicable to only one group or family of microorganisms, e.g., Facklam's scheme for identifying viridans streptococci (Ref. 3), Kloos and Schleifer's scheme for identifying coagulase-negative staphylococci (Ref. 2), Edwards and Ewing scheme for identifying gram-negative enterics (Ref. 1), etc. Each of these schemes uses test formulations that were designed especially for the metabolism and growth characteristics of the family of microorganisms the scheme addresses. Thus, a glucose fermentation test for streptococci is formulated differently than a glucose fermentation test for staphylococci and for enteric microorganisms. In fact, commercial suppliers of prepared bacteriologic media provide the above family-specific formulations on a commercial basis. The Remel (12076 Santa Fe Drive, Lenexa, Kan. 66215-3594) Catalog No. 103 (January 1994) offers microbiologists a wide variety of conventional tubed biochemical formulations with which to perform the above referenced identification schemes. The Remel catalog specifically offers eight (8) different formulations of media for detecting carbohydrate fermentation by seven (7) different families of microorganisms. They are as follows: Purple Broth is used for testing enterics (see pages 40–41), Phenol Red Broth is used for testing Streptococci (see pages 38–39), P.R.A.S. Medium and CHO Medium are used to test Anaerobes (see pages 29–30, and 40), CTA Medium and Heart Infusion Broth are used to test Fastidious microorganisms (see pages 30–31, and 33), OF Medium is used for testing Nonfermentative Gram-negative bacilli and enterics (see pages 37–38), and Yeast Fermentation Broth is used for testing Yeast (see pages 47–48).

References:
1. Ewing, W. H., 1986, "Edwards and Ewing's Identification of Enterobacteriaceae", 4th ed., Elsevier Science Publishing Co., New York.
2. Kloose, W. E., and K. H. Schleifer, 1975, "Simplified scheme for routine identification of human Staphylococcus species", *J. Clin. Microbiol.*, 1:82–88.
3. Facklam, R. R., and J. A. Washington II, 1991, "Streptococcus and related catalase-negative gram-positive cocci", p. 238–257, In A. Barlows, W. J. Hausler, Jr., K. L. Herrmann, H. D. Isenberg, and H. J. Shadome (ed.), *Manual of Clinical Microbiology*, 5th ed., American Society for Microbiology, Washington, D.C.

Beginning in the late 1960's with Roche Diagnostic's (1447 York Court, Burlington, N.C. 27215) introduction of the Enterotube Identification system for enteric bacteria and followed quickly by API's (595 Anglum Drive, Hazelwood, Mo. 63042-2395) release of the 20E Enteric Identification System, diagnostic companies began to adopt this same rationale for the development and manufacture of commercial bacterial identification kits. Vitek, MicroScan, IDS (Innovative Diagnostic Systems, 2797 Peterson Place, Norcross, Ga. 30071), and API each offer a family-specific product to identify each family or group of bacteria. (See Table I below).

TABLE I

| Microorganism | MicroScan | IDS | Vitek | API |
|---|---|---|---|---|
| Enterobacteriaceae | MicroScan Dry Overnight Gram-negative ID Panel | IDS RapID onE | Vitek GNI card | API 20E |
| Staphylococci | MicroScan Overnight Dry Gram-positive ID panel | | Vitek GPI card | API StaphIdent; API UniScept 20GP; APISTAPH |

TABLE I-continued

| Microorganism | MicroScan | IDS | Vitek | API |
|---|---|---|---|---|
| Streptococci | MicroScan Overnight Dry Gram-positive ID panel | IDS RapID STR | Vitek GPI card | API 20S; API UniScept 20GP |
| Anaerobe | MicroScan Rapid Anaerobe Panel | IDS RapID Ana | | API 20A; API Anldent |
| Yeast | MicroScan Rapid Yeast ID Panel | IDS RapID Yeast Panel | Vitek YBC card | API 20C |
| Fastidious | MicroScan HNID | IDS RapID NH | Vitek NHI | API QuadFerm |

History has taught microbiologists that the identification of clinical isolates or strains of microorganisms belonging to different families of bacteria requires the use of different conventional tube biochemical schemes or different commercial products. All traditional biochemical tests rely on growth as a means of amplifying the number of cells and inducing certain enzymes. The need to optimize the test formulae to the growth characteristics of individual families of bacteria is the basis for the historical focus on family specific tests (traditional tubed biochemical or commercial kits). For example, in the above discussion of conventional biochemical tests, there are eight different formulations for glucose fermentation formulated to be specifically reactive with seven different families of microorganisms. Because conventional biochemical tests are for the most part growth dependent, each glucose fermentation reaction has been optimized for growth of a particular family of microorganisms and for detection of glucose fermentation by that family of microorganism. This practice was carried forward by commercial biochemical identification systems, in that there are different biochemical identification products (see above list) for each of the different families or groups of microorganisms. The development of group specific product classes is both a reflection of the need to develop formulations to support family or group specific growth characteristics and to optimize substrate reactivity for the metabolism of each family or group of microorganisms. When diagnostic companies began the development of rapid identification tests that utilized chromogenic, fluorogenic or rapid conventional tests detected calorimetrically or fluorometrically, the family specific product format continued, even though the dependence on growth was greatly diminished. These new rapid ID systems were growth independent rather than growth dependent. They assay for preformed enzymes present in denser suspensions of bacteria than were used in growth-based systems.

Accordingly, it would be desirable to have a universal test system to classify and/or identify a microorganism belonging to one of any number of divergent multiple groups of microorganisms, such as by using a single battery of biochemical tests, thus, avoiding use of multiple batteries of tests or commercial test kits wherein each test battery or combination is tailored to specific groups or families of microorganisms.

SUMMARY OF THE INVENTION

The current invention for the first time creates the capability of identifying a microorganism belonging to any one of widely divergent groups of microorganisms using a single battery of biochemical tests, each with a single universal formulation. This "universal" format provides universal biochemical identification systems which produce identification results in as short an incubation time as 15 minutes, or up to 8 hours (a single work shift). The tests may be chromogenic/colorimetric, or fluorogenic/fluorometric in nature, and may be read visually or automatically. A database (probability matrix) used to classify and identify the microorganisms comprises either a single database comprising members of all families to be identified, or series of sub-databases which are specific to each family. This probability matrix is sometimes referred to hereinafter as a predetermined standard. One advantage of the present system to the user is that they need only to learn how to use a single test methodology for the majority of their microorganism identification needs. Secondly, the user need only to order and inventory a single diagnostic test, rather than to manage the inventory of multiple products, for the majority of their microorganism identification needs.

The present invention relates to single (universal) batteries of biochemical tests, i.e., test systems, for identifying one microorganism belonging to any one of a number of widely divergent groups of microorganisms. Classification of a particular microorganism in one of these widely divergent groups is largely based on the growth requirements for those particular microorganisms. For example, staphylococci, streptococci and enterococci have similar growth requirements as do enterics and nonfermenters. In the past, divergent groups of microorganisms have been detected by observing growth on well-known biochemical formulations specifically tailored to each family or group (e.g., growth media specific for yeast, anaerobic bacteria, or fastidious bacteria, etc.). Examples of widely divergent groups or families of microorganisms comprise (i) yeast and anaerobic bacteria; (ii) yeasts and *Staphylococcus sp., Streptococcus sp.*, and/or *Enterococcus sp.*; (iii) yeasts and enteric bacteria; (iv) yeasts, anaerobic bacteria, and fastidious bacteria; (v) fastidious bacteria and yeast; and (vi) anaerobic bacteria and fastidious bacteria. Examples of non-divergent groups or families of microorganisms comprise, e.g., (i) enteric bacteria and nonfermentors; (ii) *Staphylococcus sp., Streptococcus sp.*, and *Enterococcus sp.*; and (iii) Neisseria and Haemophilus.

Examples of microorganisms belonging to each of these widely divergent groups can be found in Tables II to V below. Microorganisms are added to and deleted from such groups from time to time as well as switched from one group to another or given a new name. The test systems of the present invention are applicable to all such groups.

TABLE II

| HNID Group |
|---|
| *Gardnerella vaginalis* |
| *Haemophilus haemolyticus* |
| *H. influ* Grp I |
| *H. influ* Grp II |
| *H. influ* Grp III |
| *H. influ* Grp IV |
| *H. influ* Grp V |
| *H. influ* Grp VI |
| *H. influ* Grp VII |
| *H. influ* Gr I |
| *H. p influ* Gr II |
| *H. p influ* Gr III |
| *H. p influ* Gr IV |
| *H. para/aphro* |
| *H. segnis* |
| *Branhamella catarrhalis* |
| *Neisseria cinerea* |

TABLE II-continued

HNID Group

N. flavescens
N. gonorrhoeae
N. lactamica
N. meningitidis
N. mucosa
N. sp
N. sicca
N. subflava

TABLE III

YEAST Group

| | |
|---|---|
| Blastoschizomyces capitatus | Cr. neoformans |
| Candida albicans | Cr. terreus |
| C. catenulata | Cr. uniguttulatus |
| C. guilliermondii | Geotrichum sp |
| C. humicola | Hansenula anomala |
| C. krusei | H. polymorpha |
| C. limbica | Kluyveromyces lactis |
| C. lipolytica | Pichia farinosa |
| C. lusitaniae | Prototheca wickerhamii |
| C. parapsilosis | Pr. sp |
| C. psuedotropical | Rhodotorula glutinis |
| C. rugosa | R. minuta |
| C. stellatoidea | R. rubra |
| C. tropicalis | Saccharomyces cerevisiae |
| C. tropicalis (sn) | Sporobolomyces salmonicolor |
| C. viswanathii | Torulopsis candida |
| C. zeylanoides | T. glabrata |
| Cryptococcus albidus | T. inconspicua |
| Cr. ater | T. pintolopesii |
| Cr. gastricus | Tricosporou beigelii |
| Cr. laurentii | |
| Cr. melibiosum | |

TABLE IV

Gram-Positive Group

| | | |
|---|---|---|
| Listeria monocytogenes | S. lugdunensis | Enterococcus casseliflavus |
| Micrococcus kristinae | S. saprophyticus | |
| M. luteus | S. schleiferi | Ec. avium |
| M. lylae | S. sciuri | Ec. faecalis |
| M. roseus | S. simulans | Ec. facecium |
| M. sedentarius | S. warneri | Ec. gallinarum |
| M. varians | S. xylosus | Ec. hirae |
| Pediococcus sp | Aero viridans | Ec. mundtii |
| Staphylococcus ariettae | G. morbillorum | Ec. raffinosus |
| S. auricularis | Streptococcus agalact-Gp B | Ec. solitarius |
| S. capitis | St. anginosus grp | |
| S. caprae | St. bovis | |
| S. carnosus | St. equinus | |
| S. caseolyticus | St. equisimilis | |
| S. chromogenes | St. mitis grp | |
| S. cohnii | St. mutans | |
| S. epidermidis | St. pneumoniae | |
| S. equorum | St. pyogenes | |
| S. gallinarum | St. salivarius | |
| S. haemolyticus | St. sanguis I | |
| S. hominis | St. zooepidemicus | |
| S. hyicus/chromo | | |
| S. hyicus hyicus | | |
| S. intermedius | | |
| S. kloosii | | |
| S. lentus | | |

TABLE V

Anaerobe Group

| GRAM NEGATIVE BACILLI | CLOSTRIDIA | GRAM POSITIVE BACILLI | COCCI |
|---|---|---|---|
| Bacteroides distasonis | Clostridium barati | Actinomyces israelii | Acidaminococcus fermentans |
| Bac. eggerthii | C. bifermentans | Act. odontolytic | Pepto-streptococcus anaerobius |
| Bac. fragilis | C. butyricum | Act. viscosus | Ps. asaccharolyt |
| Bac. ovatus | C. cadaveris | Bifido-bacterium dentium | Ps. magnus |
| Bac. thetaiota | C. clostridioform | Eubacterium lentum | Ps. prevotii |
| Bac. uniformis | C. difficile | Eub. limosum | Ps. tetradius |
| Bac. ureolyticus | C. histolyticum | Lactobacillus sp | Staphlococcus saccharolyt |
| Bac. vulgatus | C. innocuum | Propionibac-terium acnes | Veillonella parvula |
| Bac. splanchnicus | C. perfringens | Prop. granulosum | |
| Bifidobacterium dentium | C. ramosum | | |
| Capnocytopha sp | C. septicum | | |
| Fusobacterium mortiferum | C. sordellii | | |
| Fuso. necrophorum | C. sporogenes | | |
| Fuso. nucleatum | C. subterminale | | |
| Fuso. varium | C. tertium | | |
| Porphyromonas asaccharolyt | C. tetani | | |
| Por. gingivalis | | | |
| Prevotella bivia | | | |
| Pre. buccae | | | |
| Pre. corporis | | | |
| Pre. disiens | | | |
| Pre. melaninogen | | | |
| Pre. oralis | | | |

Methods of the present invention comprise subjecting a sample to a single battery of predetermined biochemical tests to detect the presence of at least one enzyme and/or groups of enzymes in a metabolic pathway, unique to a microorganism family, genus and/or species in order to identify the microorganism. A battery of tests is sometimes referred to hereinafter as a combination of tests or a test system. Sample as used herein includes a microorganism suspension derived from a colony grown on selective or non-selective media most preferably a suspension of a substantially pure culture.

The test systems of the present invention comprise a plurality of reaction chambers for performing the biochemical tests, wherein each reaction chamber comprises a substrate for at least one enzyme, wherein the substrate if acted on by the enzyme(s) results in formation of a detectable product in the reaction chamber and wherein the detectable products in the combination of tests are related to the identity of a microorganism in a sample.

In preferred embodiments, the reaction chambers are disposed in a single housing, e.g., a microtiter tray, herein referred to as a "panel." The number of reaction chambers in the panel can vary depending upon the particular application. The reaction chambers are open or covered, as desired.

Thus, in one aspect, the present invention provides a universal test system and methods for using the test system, to provide a single battery of predetermined biochemical tests for identifying a microorganism belonging to any one of widely divergent multiple groups of microorganisms. The microorganism is preferably classified into discrete genera and more preferably, discrete species.

In one preferred embodiment, the universal test system comprises at least one panel having disposed therein a plurality of reaction chambers, e.g., wells, containing a substrate for at least one enzyme and other components for the test. In one preferred embodiment, the single combination of predetermined biochemical tests is performed by use of a single universal test panel containing a maximum of up to about 60, more preferably between about 36 to 48 reaction chambers. In a particularly preferred embodiment, the wells are disposed in linear arrays on the test panel to facilitate use of preferred semi- or fully automated sampling, visualization, and data handling methods.

Generally, a battery of biochemical tests suitable for use in the universal test system of the present invention is selected by using known statistical techniques to identify a battery of tests capable of identifying desired multiple families of microorganisms. Different databases are then constructed. The different sets of databases are then evaluated using well known statistical techniques. One such statistical technique is described hereinafter in Example 3. The database (probability matrix) or predetermined standard used to identify the microorganisms comprises either a single database comprising members of all groups to be identified, or a series of sub-databases which are specific to each group. As previously mentioned, major advantages of this system to the user is that they need only to learn how to use a single test methodology for the majority of their microorganism identification needs and only to order and inventory a single diagnostic test, rather than to manage the inventory of multiple products, for the majority of their microorganism identification needs.

In the embodiment described above, the single database or series of subdatabases, i.e., the probability matrix is used as the predetermined standard against which results of the test system (panel) of a sample is compared to identify the microorganism. See Example 3. Preferably, the predetermined standard is generated from data obtained using spectroscopic or fluorometric techniques. However, the predetermined standard can be developed using data obtained by visual inspection of calorimetric tests as well.

A variety of biochemical tests for the identification of microbial enzymes are known in the art. Most such tests can be adapted for use in universal test system of the present invention.

The universal test systems of the present invention comprise fluorescence based tests or calorimetric based tests or some combination thereof. For example, because of greater sensitivity and speed, fluorescence based tests are preferred for some tests over calorimetric (chromogenic) based tests in the universal test system of the present invention. However, in other tests in the universal test system, calorimetric based tests are preferred because of greater convenience, such as visual test interpretation.

Thus, in one preferred embodiment of the present invention, the universal test system is capable of identifying a microorganism from multiple groups of microorganisms by using a single battery of predetermined biochemical tests, wherein the majority of tests are in a fluorescence based format. In this embodiment, the presence of enzymes and/or groups of enzymes in a pathway is detected by determining the presence of a detectable fluorescent product. In some instances, formation of the fluorescent product is a result of a pH change caused by reaction of the enzyme with a substrate (fluorometric test). In other instances, formation of the fluorescent product accompanies cleavage of a fluorogenic substrate (e.g., by hydrolysis) to form a detectable derivative fluorophore usually exhibiting increased fluorescence (fluorogenic test). In yet other instances, a chromogenic product is formed which quenches a fluorescent indicator.

Results from the battery of predetermined tests are subjected to various statistical methodologies for the purpose of identifying the microorganism in the sample, i.e., compared to at least one predetermined standard. See Example 3.

In one preferred embodiment, the detectable fluorescent product is formed in one or more of the predetermined battery of tests by cleaving at least one fluorogenic substrate (e.g., by hydrolysis) to form a derivative fluorophore with increased fluorescence. In a particularly preferred embodiment of the universal test system, esterase, peptidase and glycosidase tests are preferably conducted in a fluorogenic format.

In another preferred embodiment, the detectable fluorescent product in one or more of the biochemical tests is formed by a fluorometric indicator in the presence of an enzyme reaction. Generally, the fluorometric indicator is a pH responsive compound capable of exhibiting a change in fluorescence. Particularly, the fluorometric indicator undergoes an increase in fluorescence in the presence of an increase (alkalinization) or decrease (acidification) in pH. In a particularly preferred embodiment of the universal test system, the sugar fermentation enzyme, urease, decarboxylase, and carbon utilization enzyme tests are performed in a fluorometric format.

The present invention also provides for the first time carbon utilization enzyme tests in a fluorometric format. In this embodiment, the enzyme test comprises at least one substrate for a carbon utilization enzyme and at least one fluorometric indicator. The carbon utilization enzyme, if present, acts on the substrate and produces a pH change that forms a fluorescent product from the fluorometric indicator.

In some embodiments, the universal test system of the present invention comprises at least one calorimetric based biochemical test. The calorimetric test can be in addition to or a substitute for a test performed in a fluorescence format. In some instances, formation of the chromogenic product is a result of a pH change caused by the reaction of an enzyme with the substrate (calorimetric test). Generally, the calorimetric indicator is a pH responsive compound capable of exhibiting a change in color. Particularly, the chromogenic indicator undergoes a change in color in the presence of an increase (alkalinization) or decrease (acidification) in pH. In other instances, formation of the chromogenic product accompanies cleavage of a chromogenic substrate (e.g., by hydrolysis) to form a detectable derivative chromophore.

In a particularly preferred embodiment of the invention, the universal test system comprises at least one test for detecting each of a peptidase and glycosidase. In other preferred embodiments, the test system further comprises a sugar fermentation enzyme test. In yet other preferred embodiments, the test system further comprises at least one test for a urease, a decarboxylase, an esterase, tryptophanase (indole test) or a carbon utilization enzyme. In a panel format embodiment, a predetermined number of wells on the universal test panel each has disposed therein at least one substrate for each of the enzymes as well as other components necessary for the test. In use, the sample is added to each well, and the enzyme or group of enzymes, if present in the sample, acts on the substrate to form a detectable product. The presence of the enzyme or group of enzymes in each of the tests, if present, is determined by identifying the detectable product in each well, wherein the detectable products from the combination of tests are related to the presence of the microorganism in the sample by comparison to a predetermined standard.

In other preferred embodiments, the additional tests comprise a phosphatase test. The test for the additional enzyme is conducted in a chromogenic or fluorogenic format as desired.

In a particularly preferred embodiment, the universal test panel comprises a single battery of predetermined biochemical tests in which the tests comprise fluorescence tests for each of a peptidase, glycosidase, sugar fermentation enzyme, esterase and a carbon utilization enzyme and at least one a calorimetric test for urease, phosphatase, tryptophanase and a decarboxylase.

In a particularly preferred embodiment of the present invention, the universal test system comprises a single battery of predetermined biochemical tests that are completed in from about 10 minutes to about 8 hours, preferably from about 10 minutes to about two and a half hours. Although most biochemical tests in accordance with the present methods can be performed within about 2 hours, in some cases it is desirable to extend test times to more than three hours and up to about 8 hours. For example, in some instances test periods longer than 2 hours are used to augment detection of low levels of enzymes exhibiting slow catalysis rates. In other instances, test periods shorter than 2 hours are employed to detect abundant enzymes or enzymes with high catalytic rates.

In yet another aspect, the present invention provides fluorescent based tests useful for rapidly detecting and identifying a variety of yeasts in a sample, such as, yeasts that cause disease (e.g., Candida).

In still another aspect, the present invention provides fluorescent based carbon utilization enzyme tests.

DETAILED DESCRIPTION OF THE INVENTION

The universal test system of the present invention is conveniently configured as a panel having a predetermined number of reaction chambers or wells. Such a configuration will be used to illustrate the test systems of the present invention. This is not intended to be limiting of the universal test system, since it can be configured in a wide variety of suitable formats to meet the intended use.

Test systems of the present invention are capable of identifying a microorganism in a sample from one of multiple and widely divergent groups of microorganisms. In one preferred embodiment, the test system comprises:

a predetermined battery of non-redundant biochemical tests disposed in a predetermined number of reaction chambers, wherein each biochemical test comprises a substrate for an enzyme or a group of enzymes, and further wherein the substrate, if acted on by the enzyme or group of enzymes, results in the formation of a detectable product in the reaction chamber; and wherein the detectable products from the combination of tests are used to identify the microorganism in the sample.

By non-redundant as used herein in connection with the universal test system of the present invention is meant that the single battery of predetermined biochemical tests is not based on family-specific or group-specific formulations for each family and/or group as is known in the art. Rather, each biochemical test of the present invention is family and group independent. Preferably, a substrate is not used more than once on a panel. However, in some instances it may be desirable to include the same substrate a number of times but, e.g., in a different buffer system.

The discovery that group-specific formulations are not required to identify a microorganism in, e.g., a clinical sample, which may contain a microorganism from any one of a number of widely diverse groups is a giant leap forward, resulting in the test systems and methods of the present invention.

Formation of a detectable product as used herein preferably comprises the formation of a fluorescent product or a chromogenic product, or a change in color or in fluorescence in a reaction chamber. Other detectable products, e.g., detectable by a change in radiation or luminescence, can also be used in the practice of the present invention.

The number of tests disposed on a universal test panel of the present invention is sufficient to identify a single microorganism in a sample belonging to any one of a number of widely divergent groups. For example, if it is desired to make a universal test panel capable of identifying a microorganism from any one of the following groups: enterics, non-fermentors, anaerobes, and fastidious bacteria, the appropriate combination of tests is readily determined by, for example, following the procedure outlined in Example 3. The test selection procedure is iterative, i.e., a battery of tests is selected, run, and then challenged. If the battery fails the challenge, then the battery of tests is modified, e.g., a different substrate concentration may be selected, a test may be added or deleted, etc., run again and rechallenged and so on. To identify to the species rather than the genus level, the number of tests will be generally greater. The minimal and/or optimal number of tests for a particular use can be readily determined using known statistical techniques in accordance with the teachings herein. One example of such a technique is found in Example 3 below.

In preferred embodiments, the test systems of the present invention comprise at least one test for detecting a peptidase, glycosidase, a sugar fermentation enzyme, a urease, a decarboxylase, an esterase, a carbon utilization enzyme, a phosphatase, or a tryptophanase. In other preferred embodiments, such tests comprise a test for at least one peptidase and at least one glycosidase.

Such test systems may further comprise a test for at least one sugar fermentation enzyme; at least one urease, at least one decarboxylase, a test for at least one esterase, and at least one carbon assimilation enzyme, and various combinations thereof. In other preferred test systems according to the present invention the predetermined combination of non-redundant of biochemical tests is capable of identifying the microorganism among at least two of enteric bacteria, nonfermenting bacteria, anaerobic bacteria, yeast, *Staphylococcus sp.*, *Streptococcus sp.*, *Enterococcus sp.*, and fastidious bacteria. Another preferred test system is capable of identifying microorganism among at least one of *Staphylococcus sp.*, *Streptococcus sp.*, *Enterococcus sp.*, *Corynebacteria sp.*, *Lactobacillus sp.*, *Pediococcus sp.*, *Leuconostoccus sp.*, *Alloicoccus sp.*, *Vagococcus sp.*, *Kluyvera sp.*, *Leminorella sp.*, *Haemophilus sp.*, *Neisseria sp.*, *Moraxella sp.*, *Salmonella sp.*, *Clostridia sp.*, and *Listeria sp.*

In yet another preferred test system of the present invention the predetermined combination of non-redundant biochemical tests is capable of identifying the microorganism among at least one of anaerobes, yeast or fastidious bacteria; among anaerobes and yeast or fastidious bacteria; or among yeast and fastidious bacteria.

In other preferred embodiments, the test systems of the present invention are capable of identifying the microorganisms among at least one of Staphylococcus, Streptococcus, or Enterococcus and at least one of anaerobes, yeast, enterics, nonfermentors or fastidious bacteria or combinations thereof; among Staphylococcus, Streptococcus, and Enterococcus; among yeast, anaerobic bacteria and fastidious bacteria; or among Enterococcus, Staphylococci, Streptococci, anaerobes, yeast and fastidious bacteria.

The methods of the present invention for identifying a microorganism in a sample from among at least two groups of widely divergent microorganisms which may be present in such a sample by use of a test system comprise:
a) adding the sample to each reaction chamber comprising a substrate;
b) allowing the enzyme, if present, to react with the substrate;
c) determining the presence of the enzyme in the sample by detecting the detectable product in a test; and
d) comparing results of the combination of predetermined tests with at least one predetermined standard to identify the microorganism in the sample.

Tests for detecting carbon source utilization by a microorganism, are also provided by the present invention wherein the test comprises at least one carbon source and at least one fluorometric indicator, wherein the microorganism acts on the carbon source to produce a pH change which causes a change in fluorescence of the indicator, the change in fluorescence being indicative of carbon source utilization by the microorganism.

In a particularly preferred embodiment, the universal test panel is capable of identifying a microorganism from any one of (i) enterobacteriaceae, staphylococci, enterococci, and streptococci families and (ii) the anaerobe, yeast and fastidious bacteria groups to the level of identification desired, e.g., genus and/or species.

Typically, the volume of the reaction chamber is chosen for convenience and cost-effectiveness.

Suitable materials for use in making such panels should be substantially nonreactive with the components of the enzyme tests and includes plastics such as polystyrene, PVC and others.

In one embodiment, the universal test panels of the present invention is used to identify a microorganism belonging to any one of a number of multiple groups of microorganisms. The microorganism is identified to discrete genera and/or species, preferably to the species level.

The universal test panels of the present invention can be configured to identify bacteria and yeast e.g., bacteria from widely diverse groups such as enterics and non-fermentors; anaerobes; staphylococci, streptococci, and enterococci; and fastidious bacteria.

In one embodiment, the universal test panel includes multiple wells with different biochemical tests. However, in another embodiment, the universal test panel comprises at least one biochemical test in which the test is performed in separate wells with the same substrate but in different buffers such as TRIS, HEPES, MOPS, PIPES, histidine, phosphate, citrate, acetate, or carbonate. For example, one embodiment of the universal test panel of the present invention comprises peptidase tests using the substrate (i.e., glycylglycine 7-AMC) in Tris in one well and Hepes in another well.

Generally, the pH in each well of the universal test panel will be between about 5 to about 9. For example, peptidase and glycosidase tests are typically conducted at about pH 7–9 and about 7–8, respectively and sugar fermentation enzyme tests at about pH 7–8 and carbon utilization enzyme tests are typically conducted at about pH 5.0–6.0.

In other instances, the universal test panel comprises at least one biochemical test in which the test is performed in separate wells with isomers of enzyme substrates. In this embodiment, the isomer can be, e.g., an enantiomer, diasteriomer, or cis-trans diastereomer. Alternatively, the substrate can be a mixture of isomers. For example, $\alpha$- and $\beta$-isomers of galactose are suitable isomers for use in the sugar fermentation enzyme test. See Table VI above.

The sample to be tested on the universal test panel is a microorganism suspension obtained from a substantially pure isolate of the microorganism.

The substantially pure isolate is obtained by several well-known methods. For example, in one method, the sample is pre-cultured with a liquid, solid, or semi-solid media capable of supporting growth of a desired microorganism group. More particularly, the sample can be pre-cultured on a selective solid or semi-solid media to obtain colonies from which the substantially pure isolate of the microorganism is obtained. If desired, the substantially pure isolate can be further selected to increase numbers of desired microorganisms. In either case, the isolate is suspended in a surfactant solution to form a suspension suitable for use with the universal test panel. Typically, the suspension has a density of about 0.1 to 5 McFarland units, preferably about 0.5 McFarland units. Higher suspension densities within this range are preferable in some cases to obtain more rapid results on the universal test panel. Methods of pre-culturing samples of a microorganism are well known.

In selecting the tests for a universal test system of the present invention, a battery of these tests is selected and disposed on an appropriate panel and tested as described below to arrive at a predetermined standard (probability matrix) for use in identifying a microorganism belonging to any one of a diverse group of microorganisms.

As discussed above, a wide variety of fluorescent (e.g., fluorogenic, fluorometric), colorimetric and fluorescence quenching tests can be used in the universal test systems of the present invention.

Further, a variety of substrates are suitable for use with each of these tests. For example, in preferred embodiments of the present invention, fluorogenic and/or fluorometric tests are chosen for use with the universal test system. In these embodiments, the fluorogenic test comprises at least one fluorogenic substrate, preferably one fluorogenic substrate, that is enzymatically cleaved to form a detectable fluorescent product. In particularly preferred embodiments, the fluorogenic substrate typically consists of a substrate conjugated to a fluorogen. The fluorometric test comprises at least one substrate, preferably one substrate, that is reacted with at least one enzyme in the sample to achieve a pH change detected by a fluorometric indicator. A wide variety of suitable fluorogens and fluorometric indicators have been disclosed. See, e.g., Table VII, below, and Haugland, R. P *Handbook of Fluorescent Probes and Research Chemicals* sixth Ed. (1996) by Molecular Probes, Inc; Bascomb, S. (1987) *Methods in Microbiol.* 19, 106; Manafi, M. et al. (1991) *Microbiological Rev.* 335.

Exemplary substrates for use in the universal test systems of present invention are listed below in Table VI. Substrates 1 to 25 are fluorogenic substrates for peptidase tests. Substrates 26 to 34 are fluorogenic substrates for glycosidase tests. Substrates 35, and 37 to 54 are substrates for sugar fermentation tests using the 4-Methylumbelliferone fluorometric indicator. Substrates 55 to 60 are carbon simulation substrates. Substrates 61–62, 64–65, 73–78, 88–89, and 92 are substrates for sugar fermentation tests. Substrate 63 is a substrate for a urease test. Substrates 66–70, 79–80, and 90–91 are substrates for glycosidase tests. Substrates 71, 81–83, and 93–95 are substrates for peptidase tests. Substrates 72 and 84 are substrates for phosphatase tests. Substrates 85–87 are substrates for decarboxylase tests. Substrate 96 is a substrate for the indole test.

TABLE VI

1. L-Arginyl-L-arginine 7-AMC HCl (Tris)
2. L-Citrulline 7-AMC HBr (Tris)
3. Glycine 7-AMC HBr (Tris)
4. Glycyl-glycine 7-AMC HCl (Tris)
5. Clycyl-L-proline 7-AMC HBr (Tris)
6. L-Histidine 7-AMC (Tris)
7. L-Hydroxyproline 7-AMC (Tris)
8. L-Isoleucine 7-AMC TFA (Tris)
9. L-Leucine 7-AMC AcOH (Tris)
10. L-Lysine 7-AMC AcOH (Tris)
11. L-Methionine 7-AMC AcOH (Tris)
12. L-Serine 7-AMC HCl (Tris)
13. L-Tryptophan 7-AMC (Tris)
14. L-Arginyl-L-arginine 7-AMC HCl (Hepes)
15. L-Alanine 7-AMC TFA (Hepes)
16. Glycyl-glycine 7-AMC HCl (Hepes)
17. Glycyl-L-proline 7-AMC HBr (Hepes)
18. L-Histidine 7-AMC (Hepes)
19. L-Hydroxyproline 7-AMC (Hepes)
20. L-Isoleucine 7-AMC TFA (Hepes)
21. L-Leucine 7-AMC HCl (Hepes)
22. L-Methionine 7-AMC AcOH (Hepes)
23. L-Phenolalanine 7-AMC TFA (Hepes)
24. L-Serine 7-AMC HCl (Hepes)
25. L-Tryptophan 7-AMC (Hepes)
26. 4-MeU α-L-Fucoside
27. 4-MeU α-L-Arabinopyranoside
28. 4-MeU α-D-Mannopyranoside
29. 4-MeU α-L-Rhamnopyranoside
30. 4-MeU β-D-Fucoside
31. 4-MeU β-L-Fucoside
32. 4-MeU β-D-Lactoside
33. 4-MeU β-D-Cellobioside
34. 4-MeU N-Acetyl-β-D-Galactosamimide
35. Arbutin (acid production)
36. LOCATOR (AMC)
37. Cellobiose (acid production)
38. Dulcitol (acid production)
39. Erythritol (acid production)
40. Fructose (acid production)
41. Galactose (acid production)
42. Glycerol (acid production)
43. Inulin (acid production)
44. Lactose (acid production)
45. Maltose (acid production)
46. Melezitose (acid production)
47. Mucate (acid production)
48. Rhamnose (acid production)
49. Ribose (acid production)
50. Starch (acid production)
51. Trehalose (acid production)
52. Turanose (acid production)
53. Xylose (acid production)
54. Palatinose (acid production)
55. Acetamide (alkalization)
56. Benzoic Acid (alkalization)
57. Formic Acid (alkalization)
58. Maleic Acid (alkalization)
59. Pyrurate Acid (alkalization)
60. Malonic Acid (alkalkization)
61. Arbitol (acid production)
62. Glucuronic Acid (acid production)
63. Urea (alkalkization)
64. Mannitol (acid production)
65. Raffinose (acid production)
66. 4-MeU-β-D-Xyloside
67. 4-MeU-β-D-Glucoside
68. 4-MeU-β-D-Mannopyranoside
69. 4-MeU-β-D-N,N-Diacetyl chitobioside
70. 4-MeU-β-D-galactoside TABLE VI-continued 71. Pyroglutamic Acid (AMC)
72. 4-MeU-phosphate (pH 7-8)
73. Adonitol (acid production)
74. Arabinose (acid production)
75. Inositol (acid production)
76. Mannose (acid production)
77. Sucrose (acid production)
78. Salacin (acid production)
79. 4-MeU-N-acetyl-β-D-glucosaminide
80. 4-MeU-β-D-glucuronide
81. Arginine (AMC)
82. Glutaryl-glycl-arg (AMC)
83. Proline (AMC)
84. 4-MeU-phosphate (pH 6-7)
85. Decarboxylase buffer
86. L-Lysine (alkalkization)
87. L-ornithine (alkalkization)
88. Melibiose (acid production)
89. sorbitol (acid production)
90. 4-MeU-α-d-galactoside
91. 4-MeU-β-d-glucoside
92. glucose (acid production)
93. α-glutamic acid (AMC)
94. γ-glutamic acid (AMC)
95. tyrosine (AMC)
96. L-tryptophane (quench test)

Exemplary fluorogenic substrates for peptidases useful in the practice of the present invention comprise an amino acid, peptide, or polypeptide conjugated to a fluorogen. Examples of suitable fluorogens are shown below in Table VI and particularly include β-napthylamine and 7-aminomethylcoumarin (7-AMC). A particularly preferred fluorogen for use in the peptidase test is 7-AMC. Methods of making and using fluorogenic substrates are known in the art (See e.g., GB Patent No. 1,547,747 and EPO Patent No. 0,000,063.)

TABLE VII

| Fluorogen | Fluorogen Assay | Fluorometric Assay |
| --- | --- | --- |
| 7-AMC | X | |
| β-methylesculetin | | X |
| α-Naphthol | X | |
| β-Naphthol | X | |
| β-Naphthylamine | X | |

Suitable peptides and polypeptides for use in the peptidase assay are between about 2 and 20 amino acids in length and are arranged in a single chain, branched chain, or cyclic format. Suitable amino acids comprise the 20 common amino acids: alanine; cysteine; aspartic acid; glutamic acid; phenylalanine; glycine: histidine; isoleucine; lysine; leucine; methionine; asparagine; proline; glutamine; arginine; serine; theronine; valine; tryptophan; and tyrosine. Other suitable amino acids include rare or non-protein amino acids such as those found in fibrous proteins and certain fungal and plant toxins such as 4-hydroxyproline; 5-hydroxylysine; $\epsilon$-N-methyllysine; 3-methylhistidine; desmosine; isodesmosine; β-alanine; γ-aminobutyric acid; homocysteine; homoserine; canavanine; djenkolic acid; and β-cyanoalanine. The amino acids may be in a D or L format as desired. Exemplary substrates for use in the peptidase assay are shown above in Table VI.

In another preferred embodiment, the universal test panel of the present invention comprises at least one glycosidase test preferably performed in a fluorogenic format. In this embodiment, the glycosidase test comprises at least one fluorogenic substrate, preferably one fluorogenic substrate that is cleaved in the presence of the glycosidase in the sample. Suitable fluorogenic substrates for use in the glycosidase test comprise conjugates between a carbohydrate, typically a sugar, and a suitable fluorogen. Examples of suitable fluorogens have been described above in Table VII. A particularly preferred fluorogen is 4-MeU. Suitable sugars for use in the glycosidase test comprise about 3 to 8 carbons (e.g., a tetrose, pentose, hexose or heptose), as well as saccharides and disaccharides comprising about 2 to 10 covalently linked sugar units and a molecular weight of between about 350 to 4000 daltons. Exemplary fluorogenic substrates for use in the glycosidase assay are shown above in Table VI.

In another embodiment, a universal test panel of the present invention 20 comprises at least one test for a sugar fermentation enzyme conducted in a fluorometric format. In this embodiment, the sugar fermentation test comprises at least one sugar or saccharide such as those described above for the glycosidase test, and at least one fluorometric indicator. Examples of suitable fluorometric substrates are shown in Table VII, above and include 4-MeU. Preferably, the fluorometric indicator is capable of fluorescence in a pH range of about 6 to 8. A particularly preferred fluorometric indicator is 4-MeU. Additional substrates for use in the test include polysaccharides such as starch and glycogen with a molecular weight of between about $10^4$ to $10^6$. Exemplary substrates for use in the sugar fermentation enzyme test are shown in Table VI above.

In another embodiment, the universal test panel comprises at least one carbon utilization test conducted in a fluorometric format. In this embodiment, the carbon utilization test comprises at least one carbon source, preferably one carbon source and at least one suitable fluorometric indicator, preferably one fluorometric indicator. Fluorometric indicators suitable for use are shown in Table VII, above and include 4-MeU, and other compounds. A particularly preferred fluorometric indicator is β-methyl esculetin capable of fluorescence in a pH range of about 5 to 7.

A suitable carbon source for use in the carbon utilization test includes an alkene, alkyne, alcohol, ether, ester, nitrile, sulfide, sulfone, thiol, ketone, sulfoxide, aldehyde, amide, amine, carboxylic acid, or benzoic acid. The carbon source generally includes about 2 to 10 carbon atoms arranged in a straight chain, branched or cyclic format, having a molecular weight of between about 40 to 500. Preferred carbon sources are miscible in aqueous solutions (e.g., physiological saline and buffered solutions including Tris or Hepes) and are non-volatile. Table VI above provides examples of suitable carbon sources.

In one preferred embodiment of the present invention, the substrates of the test systems comprise lysine (AMC), leucine (AMC), methionine (AMC), glycyl-proline (AMC), Isoleucine (AMC), Trehalose, maltose, L-tryptophan (7-AMC), 4-MeU-phosphate, β-D-xyloside-4MeU, hydroxy-proline-AMC, β-D-glucuronide-4MeU, tyrosine (AMC), 4-MeU-β-D-galactoside, mannose, sucrose, and proline (AMC). In another preferred embodiment, the substrates further comprise fructose, glycerol, L-histidine 7-AMC, pyroglutamic acid (AMC) and 4-MeU-β-D-glucoside. In yet another preferred embodiment, the substrates further comprise L-serine 7-AMC, cellobiose, arginine (AMC), and 4-MeU-N-acetyl-β-D-galactosaminide.

The above-described fluorescent tests form products which are detected by conventional non-destructive instrumental fluorometric or fluoroscopic methods to quantify a fluorescent product in the tests. For example, a particularly preferred on automated instruments is a MicroScan Walkaway system commercially available from Dade MicroScan Inc. However, the universal test systems of the present invention could be adapted for use in other commercially available instruments.

In one embodiment of the present invention, the universal test panel comprises at least one test conducted in a colorimetric (chromogenic) format. For example, the peptidase, glycosidase, sugar fermentation enzyme or the carbon utilization enzyme tests disclosed herein can be conducted in a colorimetric (chromogenic) format. A variety of colorimetric tests are known for detecting peptidases such as pryoglutamyl aminopeptidases, L-alanine aminopeptidases, aryl peptidases, arylamidases; and glycosidases such as β-D-glucuronidase, β-D-galatosidase, 6-phospho-β-D-galactoside 6-phosphogalactohydrolase, α-D-galactosidase, β-D-glucosidase, neuroaminindases, α-amylase, α-glucosidase and N-acetyl-(3-D-glucosaminidase, N-acetyl-α-D-glucosaminidase, α-D-arabinosidase, β-D-fucosidase and β-D-xylosidase. Further, colorimetric tests for detecting sugar fermentating enzymes are well known and may be used in the test system of the present invention. Additional colorimetric tests suitable for use with the universal test panel include known tests for detecting e.g., ureases, oxidases, reductases, hydrolases, hydrogenases, esterases, phosphotases, tryptophanases, proteases such as chymotrypsin, decarboxylases such as ornithine and lysine decarboxylases, and enzymes capable of assimilating citric acid cycle intermediates. As described above, such tests can be adapted for use in the universal test system of the present invention and tested using probability analysis.

A calorimetric test suitable for use in the present methods can be performed in variety of detection formats. For example, in some instances, a substrate comprising a chromogen is used in a direct detection format. In this case, the chromogenic substrate can comprise, e.g., esters of o-nitrophenol, m-nitrophenol or ρ-nitrophenol, esters of indoxyl or 5-bromo-4-chloro-3-indolyl, or an aryl peptide derivative of ρ-nitroanaline. Release of the chromogen is directly detected in the calorimetric test. However, in other instances, it is desirable to conduct the colorimetric test in an indirect detection format via a suitable reagent. Examples of such a tests include chemical reaction of inorganic enzyme reaction products (e.g,. nitrate) with inorganic acids such as sulfanilic acid and α-napthylamine. In another instance, it is desirable to conduct the colorimetric test in an indirect format using a pH responsive indicator molecule to detect pH changes in the test. Examples of such molecules include bromothymol blue and phenol red. Other suitable calorimetric tests use ρ-dimethylaminocinnamaldehyde to detect release of β-naphthylamine, e.g., chromogenic peptidase tests, from chromogenic substrates comprising β-napthylamide. In yet another instance, a suitable colorimetric test may include reaction of ρ-nitroanaline derivatives with diazo compounds to enhance assay sensitivity.

Particularly, several colorimetric tests have been disclosed for detecting and identifying yeast and yeast-like microorganisms such as Protheca, as well as Neisseria, Haemophilus species, *Branhamella catarrhalis*, and *Gardnerella vaginalis*.

Table VIII below provides examples of chromogens suitable for use in a colorimetric test.

TABLE VIII

| Chromogen | Chromogen Conjugated To Substrate Through: | | | |
|---|---|---|---|---|
| | Ester Bond | Peptide Bond | Hydrogen Bonds | Glycosidase |
| phenol | x | | x | |
| α-nitrophenol | x | | x | |
| p-nitrophenol | x | | x | |
| indoxyl | x | | x | |
| α-naphthol | x | | x | |
| 4-methoxy-napthylamine | | x | | |
| hippuric acid | | x | | |
| phenolphthalein | x | | x | |
| p-nitroanaline | x | | x | |
| p-nitroanaline & diazo dye | | x | | |
| β-napthylamine | | x | | |
| p-naphthol | x | | x | |
| 6-bromo-2-naphthol | x | | x | |
| 4,6,-diamino-2 phenylindole | | | | x |
| acridine orange | | | | x |
| ethidium bromide | | | | x |

Accordingly, in one preferred embodiment of the present invention, the universal test panel comprises biochemical tests in which the tests further comprises at least one test for detecting each of a peptidase, glycosidase, sugar fermentation and carbon utilization test, preferably in a fluorescence format; and at least one calorimetric test for detecting each of urease, a decarboxylase, preferably ornithine decarboxylase and lysine decarboxylase; esterase and tryptophanase. These tests can be combined in various ways depending upon the intended use of the test system.

One preferred test system of the present invention comprises a test for at least one peptidase and at least one glycosidase. Another preferred test system further comprises at test for at least one sugar fermentation enzyme. Yet another preferred test system further comprises at least one test for a urease, a decarboxylase, an esterase or carbon utilization enzyme or combination thereof.

In another embodiment of the present invention, the universal test panel comprises biochemical tests in which the tests comprise at least one test for detecting catalase, a decarboxylase such as glutamic acid or arginine decarboxylase, an amino acid deamidase such as arginine deamidase, lipidase, pyrophosphate-diesterase, DNAse, an oxidase, an arylsulfatase, or an acetoin/diacetyl producing enzyme. In this embodiment, the tests are conducted in a calorimetric or fluorescent detection format as desired.

By the term "predetermined" as used herein is meant a biochemical test has been selected in accordance with known statistical techniques such as DFA or linear regression. An example of preferred statistical techniques are provided in Example 3. Accordingly, a "battery or combination of predetermined biochemical tests" as used herein is a group of biochemical tests that have been selected by appropriate statistical techniques.

The following non-limiting examples are illustrative of the invention.

EXAMPLE 1

Universal Test System

Substrates for use with the present invention can be made in a variety of ways. In general, the substrate formulations are designed for use in a convenient buffer, e.g., TRIS or HEPES in a pH range of between 5 and 9. Particular amounts or concentrations of substrate and buffer systems are selected to optimize the $V_{max}$ of a particular biochemical test.

More particularly, peptidase test substrates are chosen to have a final concentration of between about 0.01 to 1.0 mM. In a suitable buffer such as Tris (for example, Tris phosphate) at a Tris concentration of between about 0.1 to 1.0M. Preferably, for peptidase tests, the pH range is between about 7.5 to 8.5. Substrates are dissolved in acceptable solutions such as water, buffer, or dimethylsulfoxide (DMSO) as needed. Substrate formulations for glycosidase tests are designed in a similar manner except that the substrate concentration is generally between about 0.1 to 3.0 mM and a pH between about 7 to 8. For the carbon utilization and decarboxylase tests, performing the test in a decarboxylase buffer is preferred, although other buffers such as Tris or Hepes buffers can be used if desired. The decarboxylase buffer is formulated by combining: yeast extract (about 0.1 to 1.0% (w/v)); peptone (about 0.1 to 1.0% (w/v)); pyridoxyl-5-$PO_4$ (about 0.01 to 0.1 mM); 10% (w/v) glycerol stock (about 0.5 to 2% (w/v)); 0.02M 4-β-methylesculetin (about 0.1 to I mM); phallic acid (about 1.0 to 10.0 mM); pH 5 to 6 the amino acid or carbon source is between about 0.5 to 5% (w/v).

Sugar (acid production) tests are typically conducted in Hepes buffer or other suitable buffers (about 0.5 to 2.5 mM) at a pH of between about 7 to 8. Other components of the test include 4-MeU (about 0.01 to 0.25 mM); peptone (about 0.01 to 0.5% (w/v)); sugar (about 0.05 to 2% (w/v)); in about 1 liter of distilled deionized water.

Table VI lists exemplary substrates for use in the universal test system. The following sections (A-D) describe the formulation of particularly preferred substrates of the present invention.

In one embodiment, the substrates are disposed in a test panel such as a microtiter tray with wells (reaction chambers) arranged, e.g., in linear rows. Each reaction chamber was about 0.3 ml.

Each of the substrates was used in a biochemical test that was performed in a fluorescent or calorimetric format. Results of each test were compiled according to standard statistical techniques and compared to a database to identify, using standard microbiological culture techniques, multiple groups of microorganisms. Generally, the database used was a probability matrix that was configured, e.g., as a single database comprising members of all groups or families of microorganisms to be identified in the sample. Alternatively, (or in addition) the database is a probability matrix configured as a series of sub-databases specific to a particular group or family of microorganism in the sample. Well known statistical methods were used in constructing databases for use in accordance with the present invention (See, e.g., Example 3, below).

In general, substrate formulations for dispensing in the wells of the universal test panel were prepared in each well of a test panel to a suitable final volume, after which, the solution was dried in the well at ambient temperature. By diluting or concentrating the ingredients of the test formula, the dispense volume can be decreased or increased proportionally. In most instances, formulations were filter sterilized and refrigerated prior to dispensing.

A—Fluorogenic Peptidase Test:

A Peptidase Tris buffer (pH 8.0) was prepared. The solution was adjusted to a pH of between 7 to 9.

For substrates 1–13 of Table II above, the following substrate solutions were made in dimethylsulfoxide (DMSO) as about 0.1–0.3 mM solutions: The substrates were obtained from Sigma or Biosynth. About 5 ml of each solution was placed in a dispensing tube. The solution was brought to 500 ml with the Peptidase Tris buffer. For substrate 95, TYR concentrate was prepared by mixing about 0.01 to 0.02 g of tyrosine (AMC) in 5 ml of DMSO. For substrate 83, about 8 to 10 mg of proline (AMC) was added to about 5 ml of DMSO. Each dispensing tube was stoppered and inverted several times then racked.

Substrates 14–25 of Table VI above were prepared essentially the same as substrates 1–13, except that the substrates were diluted in a Peptidase Hepes buffer (pH 8.0). After dissolving the buffer components, the solution was brought to a pH of between about 7–9.

B—Fluorogenic Glycosidase Test:

Substrates 26–34 of Table VI above were prepared as about 0.9 mM to about 1.8 mM solutions in DMSO: Each of these substrates were obtained from Sigma.

About 5 ml of each substrate solution was added to a dispensing tube along with 10 ml of glycosidase buffer (see below). The glycosidase potassium phosphate buffer was prepared by adding Trizma base and potassium phosphate monobasic to deionized water. The solution was mixed and adjusted to a pH of between about 7 to 7.8. About 5 ml of concentrate was QS'd with the buffer to about 500 ml.

For substrate 70, a BGAL concentrate was prepared by adding about 0.3 to 0.5 g of MeU-β-D-galactoside in about 5 ml DMSO. For substrate 70, about 2–3 ml of the solution was added and brought to a final volume of about 500 ml with the glycosidase buffer. For substrates 76 and 77, sugar stock solutions were prepared by adding about 3 to 5 g of mannose or sucrose in about 1 liter of water.

C—Fluorometric Sugar Fermentation Enzyme Test:

For substrate 35 of Table VI above, a 2× arbutin stock solution was prepared by mixing about 1 to 2 g of arbutin (Sigma) in about 40 ml of deionized water (ARB stock). About 20 ml of the ARB stock was placed in a dispensing tube into which about 12.5 ml of a sugar buffer was added along with 2 ml of a 4-MeU stock solution. The solution was brought to a final volume of about 500 ml with autoclaved deionized water. The sugar buffer was prepared by mixing potassium phosphate monobasic, potassium phosphate dibasic, peptone water, to 1 liter of deionized water. The components were mixed and brought to a pH of between about 7 to 8. The peptone water solution was made by mixing lg peptone water in about 10 ml of deionized water. The MeU stock was prepared by mixing about 0.1 g of Na$^+$methyl-umbelliferone-4 in 20 ml deionized water. Substrate 36 is an AMC control lane.

For substrates 37–54 of Table VI above, the following 2× sugar stock solutions were made by individually mixing about 1 to 2 g of the following sugars in about 40 ml of distilled deionized water: Dulcitol, erythritol, fructose, galactose, glycerol, inulin, lactose, maltose, melezitose, rhamnose, ribose, trehalose, turanose, xylose or palatinose. Each of the sugars were obtained from Sigma.

Substrate 37 of Table VI above, was prepared by mixing about 1–2 g of mucic acid in about 400 ml deionized water and about 2 ml of 5N NaOH. For substrate 50, a 2× starch (STA) stock was prepared by mixing about 0.5 to 1 g of starch (Baker) with Pluronic P-104 (10% solution) in about 445 ml water.

With the exception of substrates 47 and 50 of Table VI above, about 20 mls of each 2× sugar stock solution was added to the dispensing tube followed by about 12.5 ml of the sugar base stock followed by 2 ml of MeU stock in distilled deionized water to about 500 ml. For substrate 47, about 400 ml of the MUC stock solution was added to the dispensing tube followed by about 12.5 ml of sugar buffer stock and 2 ml of MeU stock. The solution was brought to about 500 ml with autoclaved and distilled deionized water. For substrate 50, about 452.5 ml of the STA stock was added to a dispensing tube followed by about 12.5 ml of the sugar buffer solution and about 2 ml MeU stock. The solution was brought to about 500 ml with autoclave distilled deionized water.

D—Fluorometric Carbon utilization Test

Substrates 55–60 of Table VI above were prepared by making a stock solution of the appropriate carbon source. Each stock solution was prepared by adding about 12 g of the following carbon sources in about 600 ml of decarboxylase base buffer: acetamide, benzoic acid, formic acid, maleic acid, pyruvic acid, and malonic acid. Each of the carbon sources was obtained from Sigma. A dicarboxylase base solution was prepared by making a stock solution in which about 9 to 10 g of yeast extract, about 70 ml of a 2× stock solution of β-methylesculetin, about 10–20 g of protease peptone-3, about 300 ml of 10% glycerol, and about 2–4 g of phthalic acid (potassium salt) was mixed in about 2700 ml deionized water. The 2× β-methyl esculetin stock solution was prepared by mixing about 3–4 g 4-methyl esculetin in about 400 ml 2-methoxy ethanol and about 600 ml deionized water. The components were dissolved and adjusted to a pH of between 5 to 6. For substrates 55–60, 500 ml of the appropriate solution was added to a dispensing tube and dispensed.

E—Additional Tests:

A large variety of biochemical tests have been reported (see e.g., Bascomb, S. supra, and Manafi, et al. supra). Tests suitable for use in accordance with the present invention are selected by performing the methods described herein. See Example 3. In preferred embodiments, the additional tests comprise the following tests:

i) Urease—A variety of methods have been reported for detecting urease including measuring pH changes and ammonia production. See e.g., Godsey et al. (1981) *J. Clin. Microbiol.*, 13, 483; and Bascomb, S. supra.

ii) Tryptophanase (Indole test)—Several methods for detecting tryptophanase have been reported including colorimetric tests and tests based on fluorescence quenching. For example, a preferred tryptophanase test has been described previously. See, e.g., Morris et al., U.S. Pat. No. 5,173,434, herein fully incorporated by reference. See also Bascomb, S. supra.

iii) Esterase and Decarboxylase—Esterase tests can be conducted in several formats including fluorescent tests (see e.g., Manafi, et al. supra). A variety of tests for decarboxylases have been described (see e.g., Bascomb., S, supra). In a preferred embodiment, ornithine and lysine decarboxylase tests are performed by assaying formation of basic amines which increase pH and are detected by a fluorometric pH indicator such as 4-methylesculetin. In another embodiment, the decarboxylase tests are conducted in well-known calorimetric formats (see, e.g., MacFaddin, J. F. (1980) *Biochemical Tests for Identification of Medical Bacteria*, 2nd ed., Williams and Wilkins, Baltimore and London).

In use, the universal test panel is inoculated with about $10^4$ to $10^8$ CFU/ml of the sample to be tested and placed in a Walkaway (W/A) instrument, at 35° C. Sample data is collected using WADEV research software with read times at 40 minutes (baseline), 120 minutes, and 140 minutes.

Inoculum density is adjusted to a 0.08±0.01 Artel reading after inoculating wells on the panel with a RENOK® hydratorlinoculator. Results of each enzyme test are run through an ID matrix using statistical techniques to detect and identify microorganisms in the sample. A preferred statistical technique is Bayesian Probability analysis. In the examples which follow, detection and identification of samples is based on a previously generated database using pure cultures of selected yeast and bacteria species.

F) Quality Control

QC testing was performed weekly on the universal test panel and in some instances daily. All subculture plates used for database isolates were rigorously checked for purity and any contaminated plates were recultured. During testing, every effort was made to ensure the quality of the database such that raw data was rigorously reviewed and any problematic results, e.g. lack of well fluorescence, no reagent added, reaction rate of a particular strain dramatically differing from all others of the same species, were repeated or confirmed prior to inclusion in the database.

The universal test panel is tested with a variety of suitable QC isolates including those from the MicroScan RNID2, RPID, HNID, Rapid anaerobe and yeast test panels. Table IX, below, lists examples of suitable QC organisms for use with the universal test panel. Additional examples of suitable QC organisms include *K. oxytoca; A. baumannii; Sh. putrefaciens; E. coli; A. hydrophila; P. vulgaris; Ps. fluorescens; Ps. aeruginosa*. A saline solution control is typically included on the universal test panel to establish baselines to evaluate test results.

TABLE IX

| Panel | Organism |
| --- | --- |
| RNID 3 | *Acinetobacter baumanii* ATCC 49139 |
|  | *Aeromonas hydrophila* AmMS 199 |
|  | *Enterobacter aerogenes* AmMS 264 |
|  | *Esherichia Coli* ATCC 25922 |
|  | *Klebsiella oxy* ATCC 49131 |
|  | *Proteus vulgaris* AmMS 105 |
|  | *Shewanella putrefaciens* ATCC 49138 |
| ANAEROBE ID | *Candida perfringens* ATCC 13124 |
|  | *C. sordellii* ATCC 9714 |
|  | *Bacteroides fragilis* ATCC 25285 |
|  | *Peptostreptococcus magnus* ATCC 29328 |
| YEAST ID | *C. albicans* AmMS 225 |
|  | *C. pseudotropicalis* AmMS 226 |
|  | *C. tropicalis* AmMS 227 |
|  | *Cryptococcus albidus* AmMS 228 |
|  | *Cr. neoformans* AmMS 229 |
|  | *Torulopsis glabrata* AmMS 231 |
|  | *Cr. uniguttulatus* AmMS 234 |
| RPID | *Staphylococcus epidermidis* ATCC 49134 |
|  | *Enterococcus faecalis* ATCC 29212 |
|  | *Ec. durans* ATCC 49135 |
|  | *Streptococcus bovis II* ATCC 49133 |
|  | *St. pneumoniae* ATCC 49136 |
| HNID | *Neisseria lactamica* ATCC 49142 |
|  | *Haemophilus infuenzae* ATCC 49144 |
|  | *H. paraphrophilus* ATCC 49146 |
|  | *B. catarrhalis* ATCC 49143 |
|  | *Gardnerella vaginalis* ATCC 49145 |

EXAMPLE 2

Construction Of A Database

A variety of microorganisms such as yeast and bacteria can be used to construct database suitable for use with the universal test panel. For example, the following groups of microorganisms were used to construct a suitable database: HIND GROUP: *Gardnerella vaginalis; Haemophilus haemolyticus; H. influ* Grp I; *H. influ* Grp II; *H. influ* Grp III; *H. influ* Grp IV; *H. influ* Grp V; *H. influ* Grp VI; *H. influ* Grp VII; *H. p influ* Gr I; *H. p influ* Gr II; *H. p influ* Gr III; *H. p influ* Gr IV; *H. para/aphro; H. segnis; Branhamella catarrhalis; Neisseria cinerea; N. flavescens; N. gonorrhoeae; N. lactamica; N. meningitidis; N. mucosa; N. sp; N. sicca*; YEAST GROUP: *Blastoschizomyces capitatus; Candida albicans; C. catenulata; C. guilliermondii; C. humicola; C. krusei; C. limbica; C. lipolytica; C. lusitaniae; C. parapsilosis; C. psuedotropical; C. rugosa; C. stellatoidea; C. tropicalis; C. tropicalis (sn); C. zeylanoides; Cryptococcus albidus; Cr. laurentii; Cr. neoformans; Cr. uniguttulatus; Hansenula anomala; H. polymorpha; Prototheca wickerhamii; Rhodotorula glutinis; R. rubra; Saccharomyces cerevisiae; Torulopsis candida; T. glabrata; T. inconspicua; Tricosporou beigeli*; GRAM-POSITIVE GROUP: *Listeria monocytogenes; Micrococcus kristinae; M. luteus; M. lylae; M. roseus; M. sedentarius; M. varians; Pediococcus sp; Staphylococcus ariettae; S. auricularis; S. capitis; S. caprae; S. carnosus; S. caseolyticus; S. chromogenes; S. cohnii; S. epidermidis; S. equorum; S. gallinarum; S. haemolyticus; S. hominis; S. hyicus/chromo; S. hyicus hyicus; S. intermedius; S. kloosii; S. lentus; S. lugdunensis; S. saprophyticus; S. schleiferi; S. sciuri; S. simulans; S. warneri; S. xylosus; G. morbillorum; Streptococcus agalact*-Gp B; *St. anginosus* grp; *St. bovis; St. equinus; St. equisimilis; St. mitis* grp; *St. mutans; St. pneumoniae; St. pyogenes; St. salivarius; St. sanguis I; St. zooepidemicus; Enterococcus casseliflavus; Ec. avium; Ec. faecalis; Ec. facecium; Ec. gallinarum; Ec. hirae; Ec. mundtii; Ec. raffinosus; Ec. solitarius*; and ANAEROBE GROUP: *Bacteroides distasonis; Peptostreptococcus anaerobius; Bac. fragilis; Bac. ovatus; Bac. uniformis; Bac. ureolyticus; Bac. vulgatus; Bac. splanchnicus; Bifidobacterium dentium; Fusobacterium mortiferum; Fuso. necrophorum; Fuso. nucleatum; Fuso. varium; Porphyroinonas asaccharolyt; Prevotella bivia; Pre. buccae; Pre. corporis; Pre. melaninogen; C. innocuum; C. perfringens; C. sordellii; C. sporogenes; Bifidobacterium dentium; Eubacterium lentum; Eub. limosum; Propionibacterium acnes; Ps. magnus; Veillonella parvula; Ps. asaccharolyt.*

A breakdown of this particular database is as follows: ANAEROBE (54 Species), fastidious (21 Species), ENTEROCOCCI (10 Species), STAPHYLOCOCCI (28 Species), STREPTOCOCCI (14 Species), YEAST (42 Species).

To construct a database using the above-mentioned species of yeast and bacteria, about 30 isolates from each species (≈338 isolates) are tested with a battery of biochemical tests identified by well-known statistical techniques such as those disclosed in Example 3. The results of the tests are then formatted into a database (probability matrix) consisting of either a single database comprising members of all families to be identified or series of sub-databases which are specific to each family.

EXAMPLE 3

Exemplary Methods for Selecting Combinations of Tests for the Universal Test Panel The 96 non-redundant substrates of Table VI were used to generate a probability matrix as described below.

Selection of enzyme tests for a single group of microorganisms, e.g., gram negatives, is described below to illustrate this process. The same process was applied to fermentors, non-fermentors, and other groups represented by common clinical species.

A) Bacterial Isolates and Preparation:

Bacteria with conventional IDS were tested from MicroScan stock cultures.

Stock strains were subcultured twice to ensure purity and viability prior to testing. Most of the isolates tested were grown on a growth selective agar plate (e.g., MacConkey agar specific for gram-negative bacteria) incubated for about 18–24 hours at 35° C. Isolates that do not grow on one type of growth selective agar were grown on another (e.g., trypticase soy agar supplemented with 5% sheep blood plate for 18–24 hours in a non-$CO_2$ incubator at 35 ° C. for gram-negative bacteria).

Bacterial suspensions were prepared in individual tubes containing 6.5 mls of 0.4% saline with Pluronic® equivalent to a 0.5 McFarland standard using a MicroScan turbidity meter. Four separate tubes containing the same isolate were pooled into a single Renok® tray and inoculated using a MicroScan Renok® Rehydrator Inoculator. After dispensation of inocula into the panel, 3 drops of mineral oil were added to selected tests. Panels were then placed in the Walkway system for incubation at 35° C. within 30 minutes from initial inoculation into tubes.

b) Data collection and analysis:

Two MicroScan®—WalkAway Classic System, four WalkAway® 96 System, and one WalkAway® 40 were used to incubate and read these panels at all four testings. Data was collected using MicroScan research data acquisition software which allows collecting more data points, i.e. 0 minutes, 40 minutes, 120 minutes, and 140 minutes, than the Data Management System (DMS) software found on the WalkAway®. Each instrument was calibrated 2 to 3 times weekly using a MicroScan calibration panel. Raw data, collected as Artificial Fluorescence Units (AFU's) in Research Software, was then transferred in an ASCI file format to Statistical Analysis Software (SAS) using conventional floppy disks.

The biochemical tests described previously were used to generate an accurate, complete, and reliable database according to standard Bayesian probability analysis.

c) Construction of Probability Matrices

Identification agreement occurs if the combination of enzyme tests correctly identifies at species (or combined species) level with a normalized probability of ≧85% (preferably 90% or 95%) and this identification agreed with the reference identification. This is considered "Species Agreement, High Probability". If the identification at species (or combined species) level is not obtained with a probability of ≧85%, but the correct species appears as one of the possible identifications (2–5 taxa) at low probability, it is considered "Species Agreement, Low Probability" and additional tests are required to confirm species identification. In this instance, additional enzyme tests are performed to more fully differentiate the species being tested.

"Incorrect Identifications" did not meet these criteria. A "Very Rare Biotype" is obtained if the combination of tests 61 to 96 exhibits excessive deviations from expected results for the most likely taxon. A "Genus Group Identification, High Probability" is obtained if the enzyme tests do not give a species level identification at ≧85% but the sum of the probabilities for members of the same genus/group was >85%.

All data were processed and analyzed using SAS software. The raw data, collected during database testing, was converted into rate values for all tests except Indole and the decarboxylase tests using the following equation:

Rate=Final fluorescence–Initial fluorescence divided by time and multiplied by 100.

For the decarboxylase tests, the same equation was used to calculate initial rates. However, to calculate the final rate for either ornithine or lysine, the rate for the decarboxylase base was subtracted. For indole tests, Dimethylcinnamaldehyde (DMCA) was added to both an indole test well and a fluorescence control well at 2 hours and a read was taken at 2 hours and 20 minutes. A rate was assigned for this test using the following equation:

Indole Rate=Fluorescence control well–fluorescence in Indole well.

All raw and reaction rate data were reviewed for errors, i.e. duplicate entries, typographical errors, or erratic results suggesting microbiological contamination. When errors occurred, repeat or confirmation testing was carried out prior to inclusion into the database.

Individual reaction rates were then evaluated for each isolate in the database. These quantitative rate data were transformed into qualitative data to reduce the impact of inter- and intra-isolate variability. In general, the reaction rate profile was either bimodal or trimodal for a specific test, i.e. some taxa have no or low reaction rates whereas other taxa have moderate or high reaction rate values. Using a number of statistical techniques and the SAS programming language, the reaction rates for individual tests were evaluated and a numerical rate value (breakpoint) assigned to distinguish between positive and negative results. For each test, the "Separation figure" (Gyllenberg, 1963; Rypka et al., 1967; Lapage & Bascomb, 1968, La page et al., 1970) at different breakpoint values, when considered for the rates of the whole or part of the database taxa, as well as the rates observed with saline inoculated panels, were taken into consideration for selection of the breakpoint. For bimodal test results, if the reaction rate of an isolate exceeded this value the test was scored as a positive, or if the reaction rate was below this value the test was scored as a negative.

After breakpoints for individual tests were assigned, results from the combination of tests for gram-negatives were converted from a quantitative to a qualitative positive or negative value. Using different combinations of tests, different sets of probability matrices (Bascomb et al., 1973) were then constructed. The different sets of probability matrices were evaluated using the Bayesian probability identification model (Wilicox et al, 1973) for their ability to correctly identify all isolates tested and for how individual tests within each probability matrix contributes to separating ability, i.e. the ability to differentiate species. Further, tests were also evaluated for ease of manufacturing, long shelf life, ability to tolerate variance in panel setup, and elimination of oil overlay. Using all of these criteria 36 tests were selected that satisfied the above-mentioned agreement scores (see, e.g., 61–96, Table VI).

Next, the accuracy of the combination tests was evaluated. Overall, using an 85% normalized probability cutoff for acceptance of identification ("high probability identification"), the system has a combined accuracy of 98.8% (93.9% correct to species, 1.2% correct to genus, and 3.6% correct to species with additional tests) in 2 hours and 20 minutes. Examination of these same data utilizing a 90% normalized probability cutoff instead of 85% resulted in smaller number of isolates identified to the species level (30 isolates—0.9%) with a concomitant increase in the number of isolates identified correctly to the species level requiring additional testing (33 isolates—1.1%), but did not significantly decrease the number of incorrect identification (four isolates—0.1%). For this reason, 85% normalized likelihood was chosen as the cutoff value for the acceptance of identification.)

For clinically significant isolates (including 24 frequently occurring species), the combination enzyme tests 61–96 has a combined accuracy of 99.4% (97.5% correct to species with no additional tests, 1.0% correct to genus, and 0.9% correct to species with additional testing.

Further, the database results for all gram-negative fermentor species tested with the combination of tests showed a combined accuracy of 98.8% (96.5% correct to species with no additional tests, 1.1% correct to genus, and 1.2% correct to species with additional tests). Overall the system had a combined accuracy of 98.1% (86.5% correct to species, 1.4% correct to genus level, and 10.2% correct to species with additional tests).

The combination of tests identifies 119 taxa (85 fermentative species and 34 non fermentative species) in 2 hours and 20 minutes including 24 clinically significant species. Further, only 0.9% of all clinically significant taxa (less than 1 in 100 isolates commonly encountered in the clinical lab) and 3.7% of all isolates in the database require additional testing to a final current identification.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A test system for identifying a microorganism in a sample, wherein the test system is capable of identifying that microorganism from among at least two groups of widely divergent microorganisms which may be present in such a sample and wherein the test system comprises:
    a predetermined combination of non-redundant biochemical tests disposed in a predetermined number of reaction chambers, wherein each biochemical test comprises a substrate for an enzyme or a group of enzymes, and further wherein the substrate, if acted on by the enzyme or group of enzymes, results in the formation of a detectable product in the reaction chamber; and
    wherein the detectable products from the combination of biochemical tests are used to identify the microorganism in the sample.

2. The test system according to claim 1, wherein identifying a microorganism comprises classifying the microorganism to a genus or a species of microorganism or both.

3. The test system according to claim 1, wherein the predetermined combination of non-redundant tests, comprises fluorescent tests, colorimetric tests or a combination thereof.

4. The test system according to claim 3, wherein the fluorescent tests are performed in a fluorogenic or fluorometric format.

5. The test system according to claim 1, wherein the predetermined combination of non-redundant tests are performed at a temperature of between about 25° to about 37° C.

6. The test system according to claim 5, wherein the colorimetric tests are read visually or by a calorimeter.

7. The test system according to claim 4, wherein the fluorescent tests are read using a fluorometer.

8. The test system according to claim 1, comprising at least one test for detecting a peptidase, glycosidase, a sugar fermentation enzyme, a urease, a decarboxylase, an esterase, a carbon utilization enzyme, a phosphatase, or a tryptophanase.

9. The test system according to claim 8, comprising a test for at least one peptidase and at least one glycosidase.

10. The test system according to claim 9, further comprising a test for at least one sugar fermentation enzyme.

11. The test system according to claim 10, further comprising a test for at least one urease.

12. The test system according to claim 11, further comprising a test for at least one decarboxylase.

13. The test system according to claim 12, further comprising a test for at least one esterase.

14. The test system according to claim 13, further comprising a test for at least one carbon assimilation enzyme.

15. The test system according to claim 1, wherein the predetermined combination of non-redundant of biochemical tests is capable of identifying the microorganism among at least two of enteric bacteria, nonfermenting bacteria, anaerobic bacteria, yeast, *Staphylococcus sp., Streptococcus sp., Enterococcus sp.*, and fastidious bacteria.

16. The test system according to claim 1, wherein the predetermined combination of non-redundant of biochemical tests is capable of identifying the microorganism among least one of *Staphylococcus sp. , Streptococcus sp., Enterococcus sp. , Corynebacteria sp., Lactobacillus sp., Pediococcus sp., Leuconostoccus sp., Alloicoccus sp., Vagococcus sp., Kluyvera sp., Leminorella sp., Haemophilus sp., Neisseria sp., Moraxella sp., Salmonella sp., Clostridia sp.*, and *Listeria sp.*

17. The test system according to claim 1, wherein the predetermined combination of non-redundant biochemical tests is capable of identifying the microorganisms among at least one of anaerobes, yeast or fastidious bacteria.

18. The test system according to claim 17, wherein the predetermined combination of non-redundant biochemical tests is capable of identifying the microorganisms among anaerobes and yeast or fastidious bacteria.

19. The test system according to claim 18, wherein the predetermined combination of non-redundant biochemical tests is capable of identifying the microorganism among yeast and fastidious bacteria.

20. The test system according to claim 1, wherein the predetermined combination of non-redundant biochemical tests is capable of identifying the microorganisms among at least one of Staphylococcus, Streptococcus, or Enterococcus and at least one of anaerobes, yeast, enterics, nonfermentors or fastidious bacteria or combinations thereof.

21. The test system according to claim 1, wherein the predetermined combination of non-redundant biochemical tests is capable of identifying the microorganisms among Staphylococcus, Streptococcus, and Enterococcus.

22. The test system according to claim 1, wherein the test system is capable of identifying among yeast, anaerobic bacteria and fastidious bacteria.

23. The test system according to claim 1, wherein the test system is capable of identifying Enterococcus, Staphylococci, Streptococci, anaerobes, yeast and fastidious bacteria.

24. The test system according to claim 1, wherein the substrates comprise lysine (AMC), leucine (AMC), methionine (AMC), glycyl-proline (AMC), Isoleucine (AMC), Trehalose, maltose, L-tryptophan (7-AMC), 4-MeU-phosphate, 4-MeU-phosphate, tyrosine (AMC), 4-MeU-β-D-galactosidase, mannose, sucrose, and proline (AMC).

25. The test system according to claim 24, wherein the substrates further comprise fructose, glycerol, L-histidine 7-AMC, pyroglutamic acid (AMC) and 4-MeU-β-D-glucoside.

26. A method for identifying a microorganism in a sample from among at least two groups of widely divergent microorganisms which may be present in such a sample by use of a test system according to claim 1, wherein the method comprises:

a) adding the sample to each reaction chamber comprising a substrate;

b) allowing the enzyme, if present, to react with the substrate;

c) determining the presence of the enzyme in the sample by detecting the detectable product in a test; and d) comparing results of the combination of predetermined tests with at least one predetermined standard to identify the microorganism in the sample.

27. A test for detecting carbon source utilization by a microorganism, wherein the test comprises at least one carbon source and at least one fluorometric indicator, wherein the microorganism acts on the carbon source to produce a pH change which causes a change in fluoresence of the indicator, the change in fluoresence being indicative of carbon source utilization by the microorganism.

28. A test system for identifying a microorganism in a sample, wherein the test system is capable of identifying that microorganism from among at least two groups of widely divergent microorganisms which may be present in such a sample and wherein the test system comprises:

a predetermined combination of non-redundant biochemical tests comprising fluorescent tests, colorimetric test or a combination thereof, the test being disposed in a predetermined number of reaction chambers, wherein each biochemical test comprises a substrate for an enzyme or a group of enzymes, and further wherein the substrate, if acted on by the enzyme or group of enzymes, result in the formation of a detectable product in the reaction chamber, and wherein the detectable products from the combination of biochemical tests are used to identify the microorganism, wherein the predetermined combination of non-redundant tests are preformed within about 15 minutes to about 8 hours.

\* \* \* \* \*

UNITED STATES PATENT AND TRADEMARK OFFICE
CERTIFICATE OF CORRECTION

PATENT NO. : 5,888,760

DATED : March 30, 1999

INVENTOR(S) : James H. Godsey, et. al.

It is certified that error appears in the above-identified patent and that said Letters Patent is hereby corrected as shown below:

Column 3, Line 46: Delete "calorimetrically" and insert --colorimetrically--.

Column 5, Line 52: Delete "ariettae" and insert --arlettae--.

Column 7, Line 42: Delete "calorimetric" and insert --colorimetric--.

Column 7, Line 49: Delete "calorimetric" and insert --colorimetric--.

Column 7, Line 52: Delete "calorimetric" and insert --colorimetric--.

Column 7, Line 54: Delete "calorimetric" and insert --colorimetric--.

Column 8, Line 40: Delete "calorimetric" and insert --colorimetric--.

Column 8, Line 41: Delete "calorimetric" and insert --colorimetric--.

Column 8, Line 45:
  BOTH INSTANCES: Delete "calormetric" and insert --colorimetric--.

Column 13, Line 38: Delete "Galactosamimide" and insert --Galactosaminide--.

Column 15, Line 13: Delete "20".

UNITED STATES PATENT AND TRADEMARK OFFICE
CERTIFICATE OF CORRECTION

PATENT NO : 5,888,760

DATED : March 30, 1999

INVENTOR(S) : James H. Godsey, et. al.

It is certified that error appears in the above-identified patent and that said Letters Patent are hereby corrected as shown below:

Column 16, Line 43: Delete "calorimetric" and insert –colorimetric–.

Column 16, Line 52: Delete "calorimetric" and insert –colorimetric–.

Column 17, Line 11: Delete "•-nitrophenol" and insert -- o-nitrophenol --

Column 17, Line 31: Delete "calorimetric" and insert –colorimetric–.

Column 17, Line 51: Delete "calorimetric" and insert –colorimetric–.

Column 18, Line 24: Delete "lmM" and insert –1mM–.

Column 18, Line 43: Delete "calorimetric" and insert –colorimetric–.

Column 20, Line 59: Delete "calormetric" and insert –colorimetric–.

Column 21, Line 3: Delete "hydratorlinoculator" and insert –hydrator/inoculator–.

Column 22, Line 15: Delete "beigeli" and insert –beigelii–.

UNITED STATES PATENT AND TRADEMARK OFFICE
CERTIFICATE OF CORRECTION

PATENT NO : 5,888,760

DATED : March 30, 1999

INVENTOR(S) : James H. Godsey, et. al.

It is certified that error appears in the above-identified patent and that said Letters Patent are hereby corrected as shown below:

Column 22, Line 18: Delete "ariettae" and insert –arlettae--.

Column 22, Line 35: Delete "Porphyroinonas" and insert –Porphyromonas--.

Column 23, Line 14: Delete "mis" and insert –mls--.

Column 25, Line 60: Delete "calorimeter" and insert –colorimeter--.

Column 28, Line 7: Delete "test" and insert –tests--.

UNITED STATES PATENT AND TRADEMARK OFFICE
CERTIFICATE OF CORRECTION

PATENT NO.   : 5,888,760
DATED        : March 30, 1999
INVENTOR(S)  : James H. Godsey, et. al.

It is certified that error appears in the above-identified patent and that said Letters Patent is hereby corrected as shown below:

Column 28, Line 8: Delete "test" and insert --tests--.

Column 28, Line 19: Delete "preformed" and insert --performed--.

Signed and Sealed this

Third Day of October, 2000

*Attest:*

Q. TODD DICKINSON

*Attesting Officer*      *Director of Patents and Trademarks*